(12) United States Patent
Miller et al.

(10) Patent No.: US 8,224,667 B1
(45) Date of Patent: Jul. 17, 2012

(54) THERAPY ADHERENCE METHODS AND ARCHITECTURE

(75) Inventors: Deborah L. Miller, Kansas City, MO (US); Carl J. Persson, Olathe, KS (US); Thomas H. Wilson, Overland Park, KS (US)

(73) Assignee: Sprint Communications Company L.P., Overland Park, KS (US)

( * ) Notice: Subject to any disclaimer, the term of this patent is extended or adjusted under 35 U.S.C. 154(b) by 657 days.

(21) Appl. No.: 12/367,382

(22) Filed: Feb. 6, 2009

(51) Int. Cl.
*G06Q 10/00* (2012.01)
(52) U.S. Cl. .................. 705/2; 705/3; 600/300; 607/60; 340/309.16; 424/9.2
(58) Field of Classification Search ...... 705/2; 600/300; 340/309.19; 424/9.2; 607/60; 715/741
See application file for complete search history.

(56) References Cited

U.S. PATENT DOCUMENTS

| | | | |
|---|---|---|---|
| 5,933,136 A * | 8/1999 | Brown ........................... | 715/741 |
| 5,960,403 A * | 9/1999 | Brown ............................... | 705/2 |
| 5,995,937 A | 11/1999 | DeBusk et al. | |
| 6,345,260 B1 | 2/2002 | Cummings, Jr. et al. | |
| 6,389,454 B1 | 5/2002 | Ralston et al. | |
| 6,663,846 B1 * | 12/2003 | McCombs et al. ............. | 424/9.2 |
| 6,957,107 B2 * | 10/2005 | Rogers et al. ................... | 607/60 |
| 7,337,123 B2 | 2/2008 | Dvorak et al. | |
| 7,801,745 B2 * | 9/2010 | Walker et al. ....................... | 705/2 |
| 7,956,727 B2 * | 6/2011 | Loncar ..................... | 340/309.16 |
| 2002/0059082 A1 | 5/2002 | Moczygemba | |
| 2002/0116220 A1 | 8/2002 | Glazier | |
| 2002/0198454 A1 | 12/2002 | Seward et al. | |
| 2003/0036683 A1 * | 2/2003 | Kehr et al. ..................... | 600/300 |
| 2003/0144874 A1 | 7/2003 | Barret et al. | |
| 2004/0010423 A1 | 1/2004 | Sameh | |
| 2004/0122706 A1 | 6/2004 | Walker et al. | |
| 2004/0193449 A1 | 9/2004 | Wildman et al. | |
| 2004/0199412 A1 | 10/2004 | McCauley | |
| 2004/0236601 A1 | 11/2004 | Summers et al. | |
| 2004/0260577 A1 | 12/2004 | Dahlin et al. | |
| 2005/0068167 A1 | 3/2005 | Boyer et al. | |
| 2005/0102159 A1 * | 5/2005 | Mondshine ....................... | 705/2 |
| 2005/0234741 A1 | 10/2005 | Rana et al. | |
| 2006/0047552 A1 | 3/2006 | Larsen et al. | |
| 2006/0053035 A1 | 3/2006 | Eisenberg | |
| 2006/0129444 A1 | 6/2006 | Baeza et al. | |
| 2006/0161468 A1 | 7/2006 | Larsen et al. | |
| 2006/0173713 A1 | 8/2006 | Petro et al. | |
| 2006/0271399 A1 | 11/2006 | Robson, Sr. et al. | |

(Continued)

OTHER PUBLICATIONS

Dialog search.*

(Continued)

*Primary Examiner* — Dilek B Cobanoglu

(57) ABSTRACT

A therapy adherence system is provided. The system comprises at least one computer system, a database, and an application that, when executed on the at least one computer system, receives a message from a home-based patient device containing medication compliance information and physical condition information. The system also compares medication compliance information and physical condition information with a current treatment regimen and historical medication and physical condition information stored in the database. The system also calculates an updated regimen and health risk level based on at least current and historical medication compliance information and physical condition information. The system also notifies an at least one health care provider when health risk level exceeds a threshold. The system also receives response from the at least one health care provider, the response comprising adjustments to the updated regimen and a diagnosis and communicates the updated regimen.

20 Claims, 6 Drawing Sheets

U.S. PATENT DOCUMENTS

| | | | |
|---|---|---|---|
| 2007/0015974 A1* | 1/2007 | Higgins et al. | 600/300 |
| 2007/0073555 A1* | 3/2007 | Buist | 705/2 |
| 2007/0168228 A1* | 7/2007 | Lawless | 705/2 |
| 2007/0226010 A1 | 9/2007 | Larsen | |
| 2007/0282476 A1 | 12/2007 | Song et al. | |
| 2008/0005054 A1 | 1/2008 | Kurian et al. | |
| 2008/0255880 A1 | 10/2008 | Beller et al. | |
| 2008/0312959 A1 | 12/2008 | Rose et al. | |
| 2009/0164236 A1 | 6/2009 | Gounares et al. | |
| 2009/0248439 A1 | 10/2009 | Becker et al. | |

OTHER PUBLICATIONS

Google Scholar Search.*

Google Patents Search.*

Google Patent Search TM with search criteria "schedule a medical amointment symptom. OR indicatina, OR disease, OR sick", dated Mar. 30, 2011.

Kumed, "Visit Your Physician Online", 2007, http://www.kumed.com/print.aspx?page_id=2370.

Miller, Deborah L., et al., Patent Application entitled, "Health Clinic Broker," filed Jul. 23, 2008, U.S. Appl. No. 12/178,608.

Miller, Deborah L., et al., Patent Application entitled, "Health Care Delivery Optimization," filed Jul. 31, 2008, U.S. Appl. No. 12/183,893.

Office Action dated Oct. 1, 2010, U.S. Appl. No. 12/178,608, filed Jul. 23, 2008.

Final Office Action dated Apr. 5, 2011, U.S. Appl. No. 12/178,608, filed Jul. 23, 2008.

Advisory Action dated May 27, 2011, U.S. Appl. No. 12/178,608, filed Jul. 23, 2008.

Office Action dated Dec. 15, 2011, U.S. Appl. No. 12/178,608, filed Jul. 23, 2008.

Office Action dated Dec. 8, 2010, U.S. Appl. No. 12/183,893, filed Jul. 31, 2008.

Final Office Action dated Mar. 31, 2011, U.S. Appl. No. 12/183,893, filed Jul. 31, 2008.

Advisory Action dated Jun. 8, 2011, U.S. Appl. No. 12/183,893, filed Jul. 31, 2008.

Examiner's Answer dated Oct. 12, 2011, U.S. Appl. No. 12/183,893, filed Jul. 31, 2008.

* cited by examiner

FIG. 5
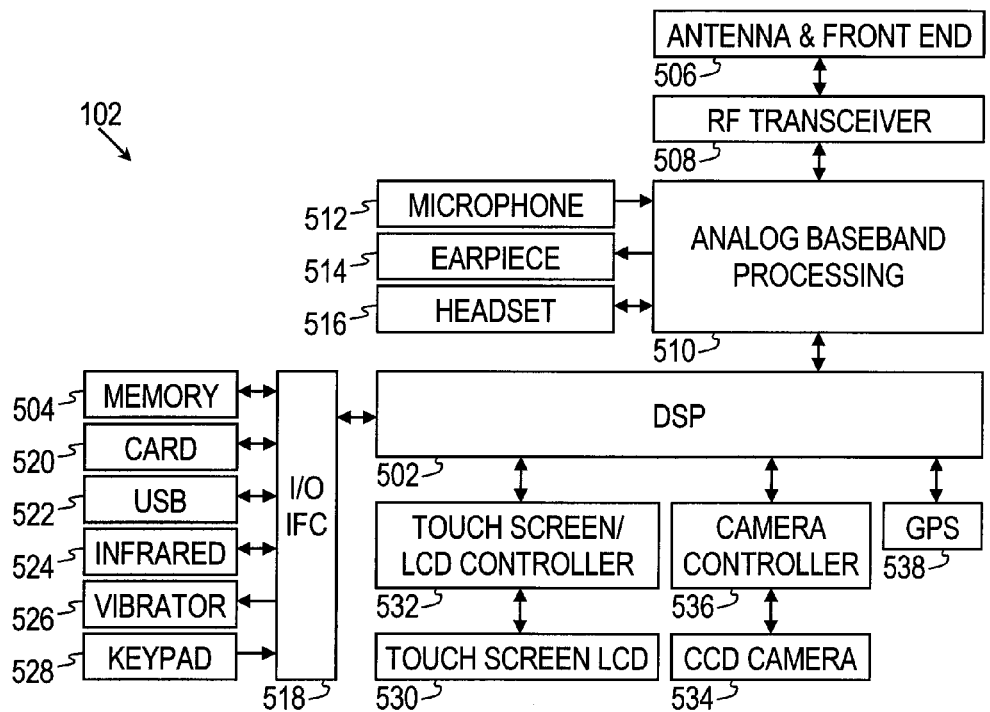
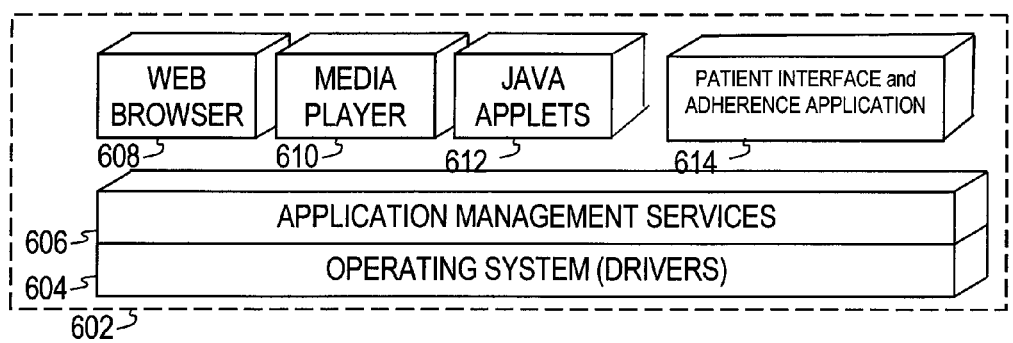
FIG. 6

content continues on next page

THERAPY ADHERENCE METHODS AND ARCHITECTURE

CROSS-REFERENCE TO RELATED APPLICATIONS

None.

STATEMENT REGARDING FEDERALLY SPONSORED RESEARCH OR DEVELOPMENT

Not applicable.

REFERENCE TO A MICROFICHE APPENDIX

Not applicable.

BACKGROUND

Many extended care patients do not take their prescribed medication in accordance with physician instructions. This problem causes a large expense due to unexpected emergency hospital admissions. An aging population, the rising cost of hospitalization, and a shortage of health care workers have driven the development of systems that can monitor patients remotely. Many elderly and disabled patients are homebound and take a large regimen of medications. When patients deviate from medication regimens that comprise a combination of medications, returning to the correct regimen may be difficult and potentially dangerous.

SUMMARY

In an embodiment, a therapy adherence system is provided. The system comprises at least one computer system, a database, and an application that, when executed on the at least one computer system, receives a message from a home-based patient device containing medication compliance information and physical condition information. The system also compares medication compliance information and physical condition information with a current treatment regimen and historical medication and physical condition information stored in the database. The system also calculates an updated regimen and health risk level based on at least current and historical medication compliance information and physical condition information. The system also notifies an at least one health care provider when health risk level exceeds a threshold. The system also receives response from the at least one health care provider, the response comprising adjustments to the updated regimen and a diagnosis and communicates the updated regimen.

In another embodiment, a processor-implemented method of encouraging therapy regimen adherence is provided. The method comprises a therapy adherence server receiving a first message from a patient device, the first message comprising patient medication regimen compliance information. The method also comprises the therapy adherence server reviewing the patient medication regimen compliance information received in the first message from the patient device against a current prescribed medication regimen to determine variances from the prescribed patient medication regimen. The method also comprises the therapy adherence server entering the received patient medication regimen compliance information into a database and the therapy adherence server determining an adjusted patient medication regimen adjusting at least one of dosage of medication prescribed and schedule for administering medication. The method also comprises the therapy adherence server sending a second message containing the adjusted patient medication regimen to the patient device and the therapy adherence server setting a timer to track compliance with the adjusted patient medication regimen.

In another embodiment, a processor-implemented method of encouraging therapy regimen adherence is provided. The method comprises a therapy adherence server receiving a first message from a patient device, the therapy adherence server calculating compliance with a medication regimen, and the therapy adherence server determining a first risk level of patient condition. The method also comprises the therapy adherence server sending a second message to at least one care provider, the second message containing the first risk level determined based on current and historical information on the patient. The method also comprises the therapy adherence server determining a second risk level of patient condition and the therapy adherence server sending a plurality of messages to the at least one care provider with increased frequency and intensity when the determined patient risk level increases.

These and other features will be more clearly understood from the following detailed description taken in conjunction with the accompanying drawings and claims.

BRIEF DESCRIPTION OF THE DRAWINGS

For a more complete understanding of the present disclosure, reference is now made to the following brief description, taken in connection with the accompanying drawings and detailed description, wherein like reference numerals represent like parts.

FIG. 5 is a block diagram of a mobile device according to an embodiment of the disclosure.

FIG. 6 is a block diagram of a software configuration for a mobile device according to an embodiment of the disclosure.

DETAILED DESCRIPTION

Figure 1:
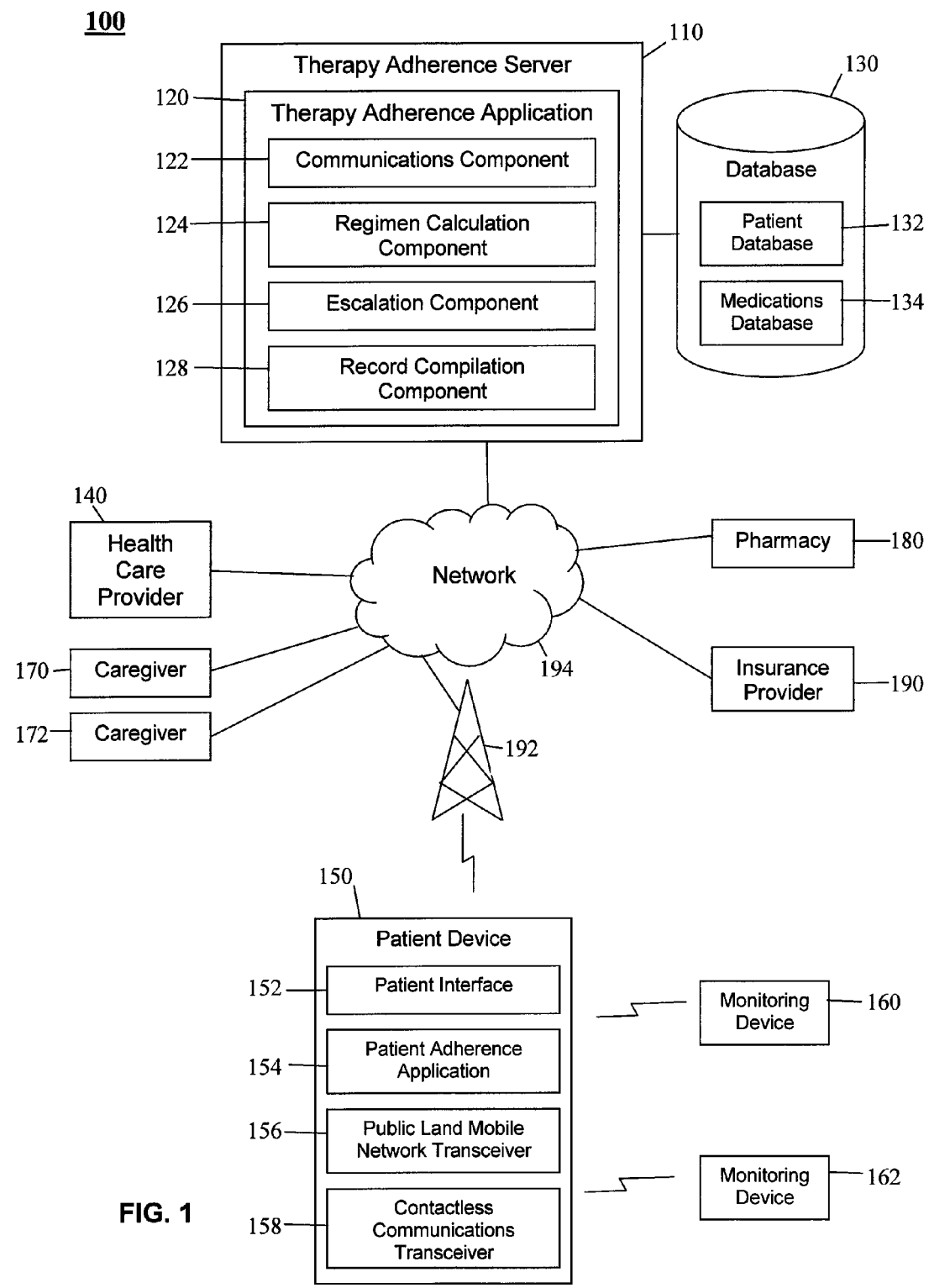
FIG. 1 is a block diagram of a system according to an embodiment of the disclosure.

It should be understood at the outset that although illustrative implementations of one or more embodiments are illustrated below, the disclosed systems and methods may be implemented using any number of techniques, whether currently known or in existence. The disclosure should in no way be limited to the illustrative implementations, drawings, and techniques illustrated below, but may be modified within the scope of the appended claims along with their full scope of equivalents.

Several embodiments of a system for therapy adherence permit a therapy adherence server to maintain periodic contact with a patient using a portable electronic device, monitor the patient's compliance with a prescribed medication and treatment regimen, and send reminders to and exchange messages with the patient. The system determines when the patient is not in compliance with the prescribed regimen and may calculate and send to the patient's device a new regimen comprising at least one of an altered dosage amount(s) and a changed schedule for administration of the dosage(s). The system may receive other information from the patient device that the patient device obtains from monitoring devices physically attached to or proximate to the patient. The system receives the medication compliance results, information generated by the monitoring devices, and other information submitted by the patient and others. The system enters the information into a therapy adherence application that recalculates and communicates the adjusted medication regimen, if necessary, and stores the patient information in a database containing the patient's medication, treatment, and health histories. The system uses algorithms and other quantitative tools to determine from the medication compliance and other information if the patient may be at risk. The system evaluates the information received from monitoring devices against historic measures and trends taken previously from the devices. The system may send questionnaires and other inquiries to the patient seeking supplemental information.

Based on current information received from the patient device and historic information stored in the patient database, the system may send escalating messages to the patient more strongly requesting compliance and/or further information. The system periodically determines a risk level for a patient and considers a plurality of current and historic information in making the determination. Based on the determined risk level, trends observed by the system, and other information specific to the patient's condition, the system may follow an escalation path to alert the patient's caregivers, for example, family members, social workers, or counselors, or the patient's health care providers including physicians, in-home health care provider, visiting nurse service, or pharmacy. The system may furnish the current and historical medication compliance information, patient medical history, and patient commentary to the health care provider. The system may in addition furnish results of its various analyses to the health care provider. The system may prompt the health care provider for a response that may include a diagnosis and altered medication regimen. The escalation plan determined as appropriate for the patient's calculated risk level and particular condition may cause the system to contact additional health care providers and/or caregivers. If the first or primary caregiver or health care provider does not respond in a timely and satisfactory manner and the patient is still determined to be at risk, the system may continue on its escalation plan by contacting additional caregivers including emergency care providers if necessary.

In non-emergency situations, an objective of the system is to maintain regular contact with a patient and assure that the patient is in compliance with the patient's prescribed medication and treatment regimen. The system additionally seeks to provide the patient's physician or other health care provider with accurate, timely, and complete information about the patient's condition and regimen compliance that will enable the physician to make good decisions about the patient's care. The system facilitates communication and movement of information between the patient and the patient's caregivers and health care providers. The system tracks the patient's medication compliance and may automatically and directly communicate with the patient's pharmacy when a prescription refill is needed, perhaps including delivery to the patient.

The system manages patient regimens that may comprise a plurality of medications. The system recalculates and balances the dosages and timetable for the various medications of a patient's treatment regimen based on the system's current observations and stored patient history as well as information contained in a pharmaceuticals database. Embodiments of the system may assist homebound or immobile patients with chronic conditions such as asthma and diabetes stay in regular contact with their providers and alert their providers if their conditions change. Patients may use scanning technology incorporated into their portable electronic devices, for example, mobile telephones, to scan a pill or pill container before taking a regular dosage. The system may send an image of the pill or pill container to the patient's mobile device as a reminder to the patient.

The system may also efficiently and expediently coordinate communication and action between a physician's office, the patient's health insurance carrier, and the patient's pharmacy when a change of therapy regimen is prescribed, the health insurer's approval may be required, and a different medication must be obtained from the patient's pharmacy and delivered to the patient on a timely basis. The ability of the system to build and analyze a long term patient history, make adjustments when medications are missed, and provide a communication link back to the patient's physician and other providers and deliver modified physician or pharmacist instructions to the patient may result in better overall care for the patient and economic benefits to pharmaceutical manufacturers, health and malpractice insurers, and pharmacies.

The historic information about medication regimen compliance and results and related health histories on a plurality of patients when compiled and analyzed may be of value to health care providers including physicians, pharmaceutical manufacturers, and health insurance providers. Noncompliance with treatment regimens including medication is very costly to society. Pharmaceutical manufacturers have difficulty securing reliable compliance data from a statistically significant quantity of patients and therefore cannot easily determine medication efficacy. Reliable compliance information and medical history data on a plurality of patients, when communicated confidentially, may be of value to pharmaceutical manufacturers and health insurers.

Turning now to FIG. 1, a system 100 of therapy adherence is provided. The system 100 comprises a therapy adherence server 110, a therapy adherence application 120, a database 130, a health care provider 140, a patient device 150, a monitoring device 160, a caregiver 170, a pharmacy 180, an insurance provider 190, a wireless base station 192, and a network 194. In embodiment, there may be more than one monitoring device 160, 162 and caregiver 170, 172. In each embodiment, the additional components described have substantially the same functionality and perform substantially the same tasks and duties as the components described.

The therapy adherence server 110 may be a computer system. Computer systems are discussed in greater detail hereinafter. The therapy adherence server 110 may comprise one computer or a plurality of computers, for example, a server farm wherein many server computers cooperate to share a processing load. The therapy adherence server 110 may comprise a plurality of computers that are located at different places, for example, to provide geographical diversity and increased service reliability. The therapy adherence server 110 executes one or more applications that provide services to at least one of the patient devices 150 including hosting of the therapy adherence application 120.

The therapy adherence application 120 executes on the therapy adherence server 110 and comprises components that provide services to patients and their providers of care. The therapy adherence application 120 comprises the communications component 122 that exchanges messages with the patient device 150 about the treatment regimen compliance of the patient using the patient device 150. The communications component 122 may send regular messages to the patient device 150 containing reminders to take specific medication and may receive regular messages in return from the patient device 150 advising that the specific medication has been taken.

Messages sent to the patient device 150 may contain images of a pill, pill container, or device to be used in administering a medication or a procedure. Messages received from the patient device 150 may contain bar code or other information associated with medication that was or will be taken. Messages received by the communications component 122 from the patient device 150 may include information taken by the patient device 150 from monitoring devices 160 either physically attached to the patient or proximate to the patient. Patient devices 150 and monitoring devices 160 may communicate using a wireless or wired link. The information may comprise glucose levels, blood pressure, blood chemistry, saliva content, or other measures provided by monitoring devices 160. Messages sent by the patient device 150 to the communications component 122 may contain content that proves or supports that a patient has taken a specific dosage of medication or performed a specific procedure. Messages sent by the patient device 150 may also contain information manually entered by the patient reporting on the patient's condition or asking questions that may be answered by the therapy adherence application 120 or forwarded by the therapy adherence application 120 to a health care provider 140, a caregiver 170, a pharmacy 180, an insurance provider 190, or other party for their response.

The communications component 122 also supports communication services between the therapy adherence application 120 and the care giving and other providers of the system 100 including the health care provider 140, caregiver 170, pharmacy 180, and insurance provider 190. The communications component 122 may contact the health care provider 140 to advise that a patient is not in compliance with the patient's medication or treatment regimen based on messages or lack of messages received from the patient device. The communications component 122 may advise the health care provider 140 that based on current medication regimen information and other information received from the patient device 150, such as glucose level, the patient may be at heightened risk and intervention by the health care provider 140 or other party may be necessary. The communications component 122 may carry messages to the health care provider 140 requesting approval for an adjusted medication regimen or it may merely advise the health care provider 140 that a new medication regimen has been calculated and sent to the patient device 150, the new regimen falling within approval limits previously set by the health care provider 140, pharmacy 180, insurance provider 190, or other party.

The communications component 122 also coordinates communication among care providers under normal conditions as well as under a potential or real emergency situation when the therapy adherence application 120 has determined that a patient is or may be at risk. The communications component 122 sends messages to caregivers 170, health care provider 140, pharmacy 180, or other parties forwarding one or more messages received from a patient device containing information about a patient condition and real or potential risk, and possibly containing alerts requesting action and response from the receiving party or parties. The therapy adherence application 120 may interpret messages received from caregivers 170, health care provider 140, pharmacy 180, or other parties and determine that additional alerting and escalation may be or is necessary.

The communications component 122 may also prompt one provider to contact another provider and follow up to certify that the prompted communication took place between the providers and certify that any follow-up communication with the patient device 150 also took place. The communications component 122 may contact the pharmacy 180 to advise that the patient is at or near the completion of a prescription and is in need of a refill. It may also prompt the pharmacy 180 to deliver the prescription to the patient if the patient is disabled, homebound, confined, or otherwise unable to travel to the pharmacy 180. The communications component 122 may coordinate communication between the health care provider 140, pharmacy 180, and an insurance provider 190 if a patient's prescription is expiring and action by the insurance provider 190 is required to renew the prescription.

In addition to originating and receiving messages, the communications component 122 may also pass communication between the patient device 150 and providers of care and record certain information passed between the parties to support the care of the patient as well as protect the providers of care and other parties from legal liability. Information contained in messages passed between components of the system 100 may be extracted from the messages and stored in the database 130 to add to a patient's history and support the patient's treatment regimen.

The therapy adherence application 120 also includes the regimen calculation component 124 that calculates a patient's medication and other regimens based on information received from the patient device 150, health care provider 140, and pharmacy 180. A function of the therapy adherence application 120 is to monitor a patient's compliance with his or her treatment regimen, including medication. The therapy adherence application 120 is regularly in contact with the patient device 150 sending and receiving messages about medication that has been taken and medication that needs to be taken. The therapy adherence application 120 also regularly receives transmission originated by monitoring devices 160 containing information about such measures as glucose level and blood pressure, for example.

When the therapy adherence application 120 detects from its messaging or lack of messaging with the patient device 150 that the patient may have deviated from the prescribed treatment regimen, including medication, it may be necessary for the regimen to be adjusted. Changes in measurements generated by monitoring devices 160 are also considered. If a patient fails to take medication on schedule, takes the wrong quantity, or a monitoring device 160 reports a significant measurement change, the regimen calculation component 124 may need to calculate a new medication regimen to adjust for the patient's mistake or negligence.

Some patients are prescribed a plurality of different medications. Combining medications can be dangerous and requires care. When a patient misses a single medication, changing the dosage amount and/or schedule for the missed medication may involve examining the other medications in the patient's regimen and make adjustments to the dosage amount and/or schedule for those other medications. If a patient's prescribed regimen involves treatment steps other than the taking of medication and calls for the performance of procedures by the patient such as drawing blood, taking a glucose level, or taking blood pressure, for example, the regimen calculation component 124 may need to recalculate the regimen for the performance of those procedures by the patient. The regimen calculation component 124 may also be required to engage a health care provider 140, pharmacy 180, and/or insurance provider 190 for advice or approval in making an adjustment to a treatment regimen including a medication regimen.

The regimen calculation component 124, in adjusting treatment regimens, may access the database 130 for information about medications, combinations of medications, pharmacology, contraindications, and patient allergies to medications. The regimen calculation component 124 may draw upon the medical history of the subject patient stored in the database 130 and it may examine confidentially compiled medical histories of other patients with similar conditions for input on adjusting a treatment regimen. The regimen calculation component 124 may also draw on sources of pharmaceutical and other health care information stored in databases or other locations not part of the system 100.

In an embodiment, the regimen calculation component 124 may not make final adjustments to patient treatment regimens without the approval of the subject patient's health care provider 140. As prescription medications are the legal responsibility of the prescribing physician or other authorized professional, the regimen calculation component 124 may function in an advisory role to a health care provider 140, assembling proposed medication regimens to address the subject patient's condition with the final approval of the health care provider 140 required. In an embodiment, the regimen calculation component 124 may be authorized to adjust medication regimens within certain limits or ranges without approval of the health care provider 140 with adjustments outside of those predetermined limits or ranges requiring approval.

The therapy adherence application 120 also comprises an escalation component 126 that detects when messages received from a patient device 150 indicate that a patient may be at heightened risk. The communications component 122 contains functionality to advise the escalation component 126 that the patient is persistently and perhaps dangerously not in compliance with the patient's prescribed treatment regimen. The escalation component 126 may calculate a risk level for a patient based on one or more algorithms that examine the patient's prescribed treatment regimen, changes in patient compliance, measurements provided by monitoring devices 160 and the patient, and the patient's medical history. The risk level may be a composite measure taking these factors into account, applying weights and other statistical procedures to these factors, and considering other factors such as the patient's age, general health, and body weight, for example.

The escalation component 126 may gather subjective data from the patient device 150 as part of addressing a potential patient problem. In an embodiment, the therapy adherence application 120 may, for example, provide a questionnaire to the patient device 150 asking questions about the patient's overall feelings, diet, and recent changes in habits or general health. Responses received from the patient device 150 are entered into the database 130 and made part of any risk determinations and escalation decisions.

The escalation component 126 examines the patient's determined risk level and other information received from monitoring devices 160, 162 and directly from the patient, the patient's current and past treatment regimens, the patient's immediate and past conditions, and other relevant information to determine additional steps, if any, to provide care to the patient and reduce risk to the patient and others. When medication is not being taken as scheduled, the escalation component 126 may send escalating alerts to the patient device 150. Before contacting the patient's health care provider 140, the escalation component 126 may initially contact a caregiver 170 with a request to call or visit the patient and provide a response on a timetable. If the patient's condition is determined by the escalation component 126 to worsen after one or more caregivers 170 have been engaged and reported results of their contact with the patient, the escalation component 126 may then contact the patient's health care provider 140 and require a response by a certain time. The response may include an adjusted treatment regimen with an adjusted schedule for the therapy adherence application 120 to monitor the patient. The escalation component 126 may work with the communications component 122 to coordinate communications between two or more health care providers 140, caregivers 170, and pharmacy 180 to make certain that appropriate action is taken including contact made with the patient and appropriate follow up is made.

The escalation component 126 may pursue any one of a plurality of escalation paths given the risk levels it calculates for a patient and the responses it receives from the various components of the system 100 it calls upon for assistance. The escalation component 126 may pursue certain actions deemed necessary when a provider of care does not take requested action or is delinquent in responding. In critical situations, if the escalation component 126 determines that a patient is experiencing significantly heightened risk and is not receiving action from providers called upon, the escalation component 126 may contact emergency medical providers, law enforcement departments, or other agencies to contact and possibly visit the patient.

The therapy adherence application 120 also comprises a record compilation component 128 that manages current and historical patient, medication, regimen, and other information in the database 130. Building a complete patient file is a key element in developing and managing patient treatment regimens. Patient devices 150 and monitoring devices 160 generate valuable information about patients and their conditions that may be used by the components of the therapy adherence application 120 as well as health care providers 140, caregivers 170, and others in diagnosing conditions and prescribing treatment. In an embodiment, the database 130 contains medical records and current and historical treatment regimens on a plurality of customers. The regimen calculation component 124 may draw upon the compiled records of a plurality of patients with similar conditions and medical histories in determining a regimen for a patient. The aggregated and analyzed records of the plurality of patients may have value in determining the correct medication regimen for a patient.

Pharmaceutical manufacturers, universities, and government researchers have difficulty securing a statistically significant body of reliable data about patient usage of medications. Gathering data from individual patients about their use of medications and the results of their treatment is expensive and time consuming but is essential in determining the efficacy of medications. For empirically gathered data to be useful to a pharmaceutical manufacturer or researcher, the data usually must be collected over an extended period from a large body of patients. The therapy adherence application 120 may be able to gather a large body of data over an extended period of time that is useful and may be made commercially available. The record compilation component 128 of the therapy adherence application 120 may draw treatment regimen and patient medical history data from the database 130, apply statistical techniques to the data, perform analyses, and package the data for use by a pharmaceutical manufacturer, university, or government researcher.

The database 130 stores information about patients using patient devices 150 whose treatment regimens are being monitored by the therapy adherence application 120. The database 130 also stores information about medications and treatment devices and procedures used by patients. The database 130 may be a collection of several databases separately storing information gathered and used by the therapy adherence application 120 in promoting care. The database 130 comprises the patient database 132 that contains the current and past treatment regimens, including medication regimens and results of those regimens for patients associated with the system 100. The patient database 132 also includes patient medical histories that include a chronology of patient conditions, patient health, and medical information. The information may be supplied by the patient, health care providers 140, caregivers 170, the pharmacy 180, the insurance provider 190, and/or others. The information is used primarily for providing the patient with good health care but information from the patient database 132 may also be used, within privacy limitations, to assist in determining the care for other patients, as well as be compiled and commercially supplied to parties outside of the system 100 for their use in research, determining medication efficacy, and securing regulatory approval of their pharmaceutical products and treatment methods.

The database 130 also comprises the medications database 134 that contains information about medications that may be prescribed by health care providers 140. The information includes the conditions the medications are indicated for, recommended dosages and methods for administering, contraindications, potential adverse reactions, and other information required by law. The medications database 134 may contain information made publicly available by pharmaceutical manufacturers, researchers, and government agencies and it may contain information gathered and compiled by components of the system 100. The database 130, the patient database 132, and the medications database 134 may be implemented in a variety of manners known to those skilled in the art, including as a relational database, as an object-oriented database or according to some other data storage/access principles.

The health care provider 140 is the patient's physician or other professional provider of medical services. The health care provider 140 may be an individual physician, physicians assistant, medical group, clinic, or hospital with the authority to write and adjust medication and other treatment regimens involving prescription drugs.

The patient device 150 is a portable electronic device in the possession of the patient and used by the patient to exchange messages with the communications component 122 of the therapy adherence application 120 about the patient's treatment regimen and medical condition. The patient device 150 may be a mobile telephone, personal digital assistant (PDA), or other portable electronic device capable of engaging in two-way communication. The patient device 150 comprises a patient interface 152 through which the patient reads information sent by the communications component 122 and enters information to be transmitted to the therapy adherence application 120 and possibly beyond to care providers and other components of the system 100. The patient interface 152 may be a series of graphical user interface (GUI) screens that the patient uses to view static content such as images of pills and pill containers sent by the therapy adherence application 120. The patient interface 152 may provide the patient access to interactive content that the patient may use to respond to questions sent by the therapy adherence application 120 by entering text- or voice-based responses or view video content provided by a pharmaceutical manufacturer, for example. In an embodiment, the patient interface 152 may be used for the therapy adherence application 120 to conduct a live video conference between the patient and a health care provider 140, caregiver 170, or other party as long as the patient device 150 and the equipment used by the counterparty have the requisite video transmission hardware and software.

The patient device 150 also comprises the patient adherence application 154 that is the client-side functionality of the therapy adherence application 120. In an embodiment, certain functionality of the components of the therapy adherence application 120 may reside and execute on the patient device 150. Sounding regular alerts to the patient, processing and responding to some inquiries entered by the patient, storing information entered by the patient for later transmission to the therapy adherence application 120, and determining the correct therapy administration training video to play for the patient are examples of functionality that need not reside on the therapy adherence server 110 and may instead execute partially or entirely by the patient adherence application 154. In embodiments, a patient in possession of his or her patient device 150 may be out of transmission range of the wireless network used by the system 100. The patient may be prompted regularly to take medication and enter information into the patient device 150. The functionality of the patient adherence application 154 allows the patient to receive this basic functionality while unable to exchange transmissions with the communications component 122.

The patient device 150 also comprises a public land mobile network (PLMN) transceiver 156 that allows the patient device 150 to make wireless signal contact with a wireless base station 192 to engage in voice and data communications with other components of the system 100 and parties that are not components of the system 100. The patient device 150 may also comprise a contactless communications transceiver 158 that communicates with a monitoring device 160 to enable the monitoring device 160 to send diagnostic data to the patient device 150 for transmission by the patient device 150 to the therapy adherence application 120. In an embodiment, the monitoring device 160 may send data to the patient device 150 using a wired communication link. The contactless communications transceiver 158 may obtain the information from the monitoring device 160 using radio frequency communication that may include near field communication (NFC) technology, infra-red, ultra-sonic, optical, radio frequency, wireless, Bluetooth, Wi-Fi, and other communication links that do not involve direct physical contact. The patient device 150 may also comprise functionality permitting it to scan, photograph, and transmit images including barcodes and radio frequency identification tags attached to objects.

The monitoring device 160, 162 is physically attached to, proximate to the patient, or otherwise accessible to the patient and the patient device 150. The monitoring device 160, 162 may be a blood pressure monitor, glucose meter, weight scale, pulse oximeter, spirometer, electrocardiogram, or other patient monitoring equipment that may be used in a patient's home. The monitoring device 160, 162 may be equipped with near field communication technology allowing it to send information to the patient device 150 including the results of tests or observations made by the monitoring device 160, 162.

The caregiver 170, 172 is a party responsible for monitoring the care of the patient. The caregiver 170 may be a family member that may or may not reside with the patient. The caregiver 170 may regularly carry a portable electronic device that permits the caregiver 170 to engage in two way communication with the therapy adherence application 120 and the patient device 150. The caregiver 170 may be the first party contacted by the therapy adherence application 120 when the patient is not or may not be in compliance with his or her current treatment regimen and the patient device 150 is not sending messages or responding to alerts. In an embodiment, the caregiver 170 may be a social worker, counselor, in home health care provider, visiting nurse service responsible for care of a patient that is disabled, a person in extended rehabilitation from surgery or injury, a senior citizen, or a minor without suitable adult care. In an embodiment, the patient may not be an individual in need of medical care but may instead be an individual confined to residence or other location and required to take medication under a court decree and supervised by a court-appointed counselor or parole officer. In the embodiment, the caregiver 170 is the court-appointed counselor or parole officer and is notified by therapy adherence application 120 when the patient, parolee, or probationer is not in compliance with the court-mandated treatment regimen.

The pharmacy 180 is the patient's supplier of prescription medication, non-prescription medication, and treatment devices. In an embodiment, the pharmacy 180 may be a chain of pharmacy retailers. In an embodiment, the pharmacy 180 has the capability to deliver new or refilled prescription orders to the patient who may be disabled or homebound.

The insurance provider 190 is the patient's provider of health insurance coverage and may be a party for communications about changes in a patient's treatment regimen. In an embodiment, the insurance provider 190 may need to review and approve changes to a regimen proposed by the patient's health care provider 140.

The wireless base station 192 may be any of a cellular wireless base station, for example a Code Division Multiple Access (CDMA), Global System for Mobile Communications (GSM), and/or Universal Mobile Communications System (UMTS) cellular wireless base station; a World-wide Interoperable Microwave Access (WiMAX) base station; a WiFi access point; or other wireless access device.

The network 194 promotes communication between the components of the system 100. The network 194 may be any communication network including a public data network (PDN), a public switched telephone network (PSTN), a public land mobile network (PLMN), a private network, and/or a combination thereof.

Figure 2:
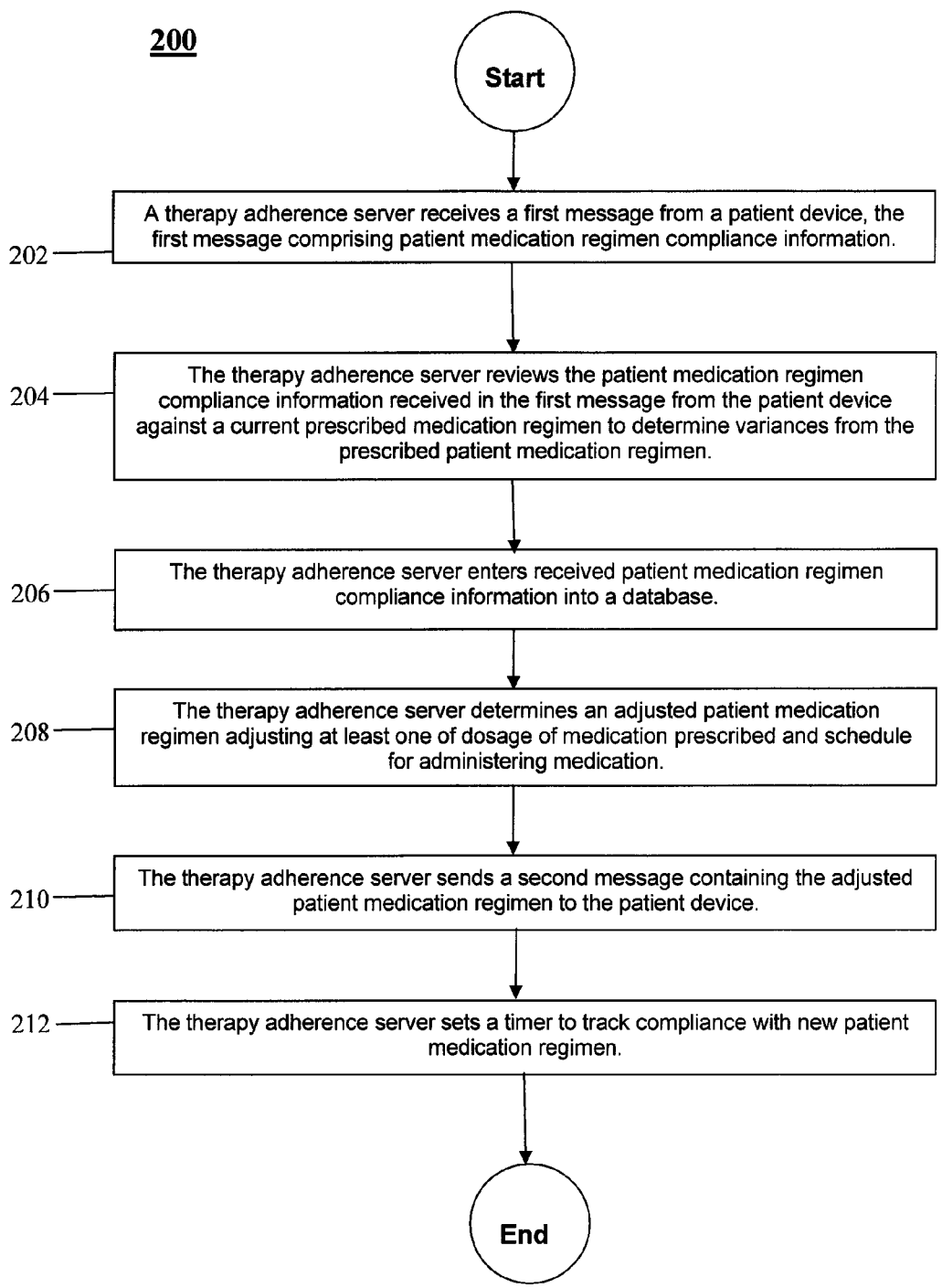
FIG. 2 is a flow chart illustrating a method according to an embodiment of the disclosure.

Turning now to FIG. 2, a method 200 is provided for enforcing a therapy adherence regimen. Beginning at block 202, the communications component 122 of the therapy adherence application 120 receives a message from the patient device 150. The message contains a report detailing the patient's compliance with his or her medication regimen and/or other treatment regimen. The message may also contain information originated by monitoring devices 160, 162 about the patient's blood pressure, glucose level, or other measures taken by the monitoring devices 160, 162. In an embodiment, the patient may have manually entered the information about medications taken into the patient interface 152 of the patient device 150. In another embodiment, the patient may have used the patient device 150 to photograph or scan an image of the medication or the medication container and sent the image to the therapy adherence application 120. In an embodiment, the patient may have used the patient device 150 to photograph or scan a barcode, ShotCode, or radio-frequency identification (RFID) tag attached to the medication or medication container and sent the image to the therapy adherence application 120. The patient device 150 may be sending the regimen compliance information and monitoring device reporting to the therapy adherence application 120 as a result of an alert generated by the therapy adherence application 120, by the patient adherence application 154 executing on the patient device 150, or as a result of another component contacting the patient device 150.

At block 204, the therapy adherence application 120 reviews the medication regimen compliance information contained in the message received at block 202 against the current prescribed medication regimen for the patient. Any information originated by monitoring devices 160, 162 and included in the message may be reviewed and compared with historical measures originated by monitoring devices 160, 162 and stored in the patient database 132. Any additional information provided by the patient, such as responses to other inquiries sent by the therapy adherence application 120 on behalf of the patient's health care provider 140 or caregivers 170, 172, may also be reviewed. The therapy adherence application 120 analyzes the information contained in the message from the patient device 150, performs statistical analysis on the information received in the message and relevant historical information on the patient medication compliance and medical history.

The therapy adherence application 120 examines its analysis for trends and signals indicating that the patient may be missing medications or taking medications on the wrong schedule. In an embodiment, the patient may be fully in compliance with his or her prescribed therapy adherence regimen that may include medication, exercise, diet, and use of monitoring devices 160 but exhibit symptoms that indicate the patient's condition is not improving as expected or is in fact worsening. A function of the therapy adherence application 120 includes identifying these situations in which a compliant and cooperative patient may need different or additional care because the prescribed treatment regimen is incorrect or inadequate for the patient's particular condition.

At block 206, the therapy adherence application 120 stores the information received in the message received from the patient device 150 at block 202 in the patient database 132. The therapy adherence application 120 also stores, in the patient database 132, the results of any analysis it performed at block 204 as well as input received from health care providers 140, caregivers 170, 172, and others relevant to the contents of the message received at block 202 and the results of the analysis of the information contained in the message.

At block 208, the regimen calculation component 124 determines that the patient's therapy regimen needs to be adjusted in response to observations and results of analysis performed on data received in the message from the patient device 150, information previously stored in the patient database 132, and relevant information received from the patient's care providers. The patient may have made an honest or negligent mistake in the dosage amount taken or timetable for one or more medications. Information generated by a monitoring device 160 may have caused concern. The patient may alternatively be fully compliant but exhibit a worsening, perhaps improving, or otherwise changing condition. The regimen calculation component 124 calculates the new medication and other treatment regimen for the patient based on this information.

When a patient has been prescribed a plurality of medications and misses or delays taking one or more medications as scheduled or takes the incorrect dosage, calculating the patient's new regimen may require adjusting the dosage and amount for more than just the one or more medications that were taken incorrectly. The regimen calculation component 124 draws upon information in the medications database 134 and other reliable sources in making any adjustments to a patient's medication regimen. In an embodiment, the regimen calculation component 124 may obtain acknowledgment from the patient's health care provider 140 with final responsibility for prescriptions before issuing the adjusted treatment regimen to the patient device 150. If necessary, the therapy adherence application 120 may also obtain approval from the patient's insurance provider 190 for the adjusted regimen and may contact the pharmacy 180 to arrange preparation and perhaps delivery of new medication to the patient. In the event any of those parties delay in their response in a manner that poses a risk to the patient, the escalation component 126 may be engaged for moving the situation to the next level of alert and action.

At block 210, the communications component 122 sends the adjusted treatment regimen to the patient device 150 and may prompt the patient device 150 for acknowledgement that the message was received and that the adjusted treatment regimen is understood. The communications component 122 may also send messages to the health care provider 140, caregivers 170, 172, pharmacy 180, and insurance provider 190 confirming for those parties that the adjusted regimen is fully approved and has been activated for the patient.

At block 212, the therapy adherence application 120 sets a timer to conduct follow up messaging with the patient device 150 to determine that the patient has properly commenced the adjusted treatment regimen. In an embodiment, the therapy adherence application 120 may also take steps to make certain that monitoring devices 160, 162 that received changed instructions arising from the change of treatment regimen are following those instructions and generating reporting as instructed.

Figure 3:
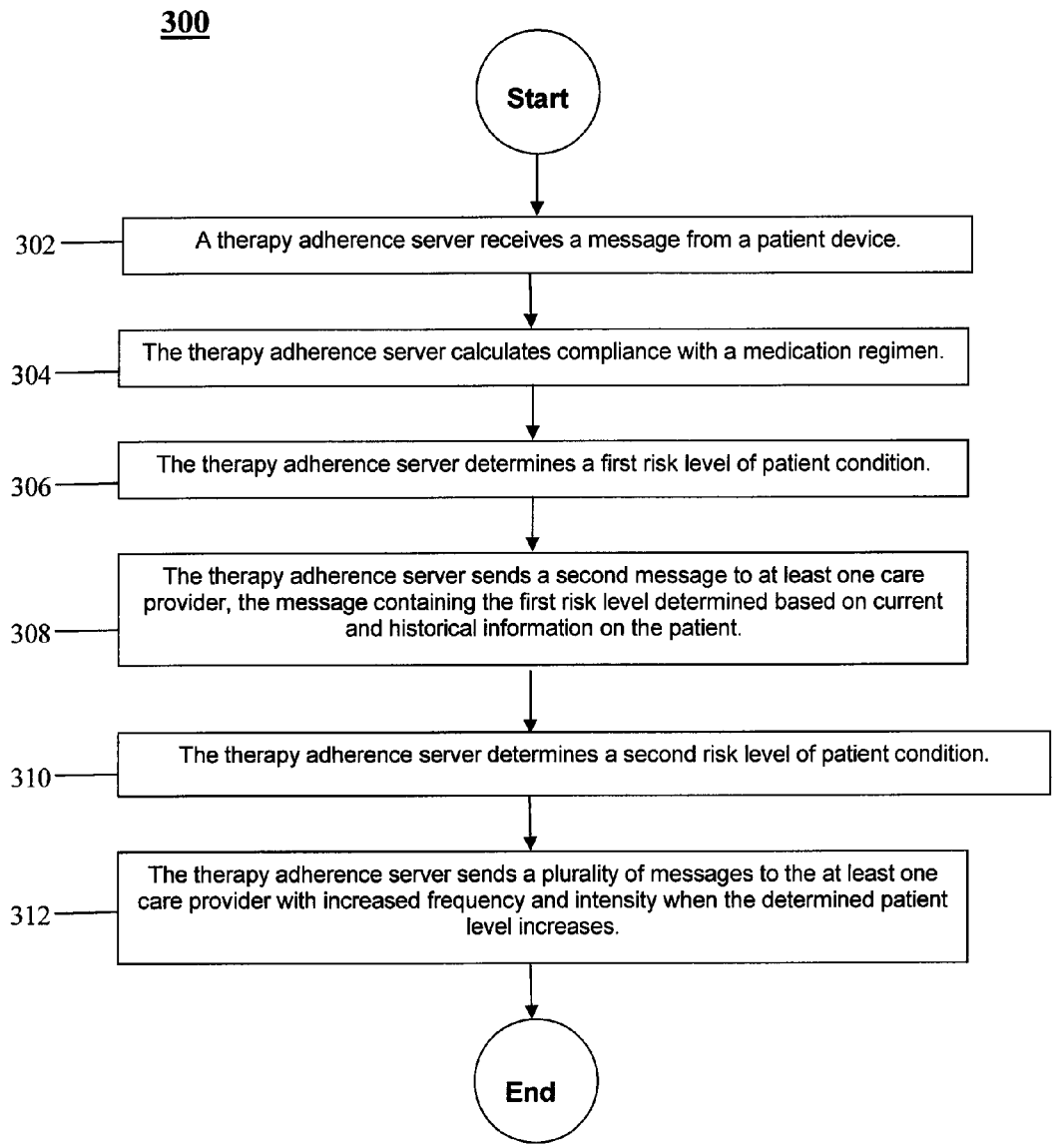
FIG. 3 is a flow chart illustrating another method according to an embodiment of the disclosure.

Turning now to FIG. 3, a method 300 of enforcing a therapy regimen is provided. The method 200 was primarily concerned with situations wherein a patient may need an adjustment in his or her treatment regimen due to an oversight in taking a dosage or information from a monitoring device 160, 162 or the patient indicates that an adjustment is necessary. In such situations that may be commonplace when the therapy adherence server 110 is administering therapy regimen programs for a large quantity of patients, the regimen calculation component 124 may be able to routinely and safely make adjustments to treatment regimens with a low level of involvement by health care providers 140 and other providers of care. By contrast, the method 300 is concerned with situation in which a patient's condition may be changing for the worse, perhaps radically so, and rapid and active involvement by the patient's health care provider 140 and other care providers may be necessary.

Beginning at block 302, the communications component 122 of the therapy adherence application 120 receives a message from a patient device 150 containing information about the patient's compliance with the patient's current treatment regimen. As with block 202, some contents of the message may also have been originated by a monitoring device 160 and been entered manually by the patient. As was performed at block 204, the therapy adherence application 120 at block 304 reviews the medication regimen compliance information contained in the message received at block 202 against the current prescribed medication regimen for the patient to calculate compliance. Information provided by monitoring devices 160, 162, for example glucose levels, is also analyzed. Historical treatment compliance and patient health information stored in the patient database 132 may also be examined.

At block 306, the therapy adherence application 120 determines a risk level of the patient's condition. Determining a patient risk level may be a step that is performed every time a patient device 150 furnishes data to the therapy adherence application 120. While this step was not defined previously in the method 200, determining a patient's level of risk was implicit in that method and may be monitored no matter how healthy a patient may appear. At block 306, the risk level of the patient is determined. This determination may be made by entering a plurality of data into algorithms and health maintenance software available to the therapy adherence application 120. The process examines the patient's current and historic compliance with therapy regimens, current and historic data reported by monitoring devices 160, 162, trend analyses of these measures, historic health information in the patient database 132, responses by the patient to questions provided the patient device 150, and any input from the health care provider 140 or other providers of care. Determining risk level may not be as simple as arriving at a single composite measure by the therapy adherence application 120. How factors combine with each other and the trends discerned when those factors are examined may also have a bearing on determining patient risk.

At block 308, the communications component 122 sends a message to the patient's providers of care including the health care provider 140, caregivers 170, 172, and perhaps pharmacy 180 indicating that a new risk level for the patient has been determined. This message may also include advice that an adjusted treatment regimen is also recommended. The new risk level may have been calculated because the patient has persistently missed or incorrectly taken medications. More alarmingly, the new risk level may have been caused by a change of measure originated by a monitoring device 160, 162 and forwarded by the patient device 150. A combination of an adverse monitoring device measurement and failure to take medication properly or at all by the patient may cause a patient risk level to escalate. The escalation component 126 of the therapy adherence application 120 is engaged to determine an escalation plan given the newly determined risk level of the patient as well as specifics of the patient's situation including the patient's ailment or ailments and historical patient medical information extracted from the patient database 132. The escalation plan is a set of steps to be taken by care providing components with further steps contingent upon action taken by the care providing components and the results derived from further observation of the patient's condition.

The escalation component 126 and the communications component 122 work in tandem to notify the patient's care providers of the need for their action and response. A caregiver 170, 172 such as a family member, social worker, or counselor may initially be tasked with contacting or visiting the patient and reporting back to the therapy adherence application 120. After further messages are received from the patient device 150 reporting on regimen compliance, the escalation component 126 may engage caregivers 170, 172 again for further involvement and reporting. The escalation component 126 may engage the patient's health care provider 140 for its involvement in contacting the patient device 150 and coordinating activity with one or more caregivers 170, 172. The therapy adherence application 120 may maintain persistent and direct communication with the data processing systems of the health care provider 140 and some caregivers 170, 172 so that contact is instantaneous. The escalation component 126 determines the action that is necessary depending on what has occurred to the moment regarding provider response and the information it is receiving from the patient device 150.

At block 310, the therapy adherence application 120 determines the patient's risk level again. As a patient medical crisis may be escalating, the escalation component 126 may more frequently determine the risk level of the patient and may apply different criteria in making its determination. In escalating situations, at block 312, the escalation component 126 will send more frequent and persistent alerts to health care provider 140, caregivers 170, 172, and others while monitoring patient condition until it receives reliable reporting that the patient condition is stabilizing and the level of care received is appropriate for the ailment and severity of the patient's condition. If the escalation component 126 determines that alerts to health care provider 140, caregivers 170, 172, and others are not receiving responses commensurate with the risk level of the patient, the escalation component 126 may take further steps, such as contacting emergency medical providers and law enforcement agencies if necessary. The escalation component 126 may also maintain persistent direct links with the patient's pharmacy 180 if a new medication regimen is determined to be indicated and the medication may need to be delivered to a homebound patient. The actions of the escalation component 126 may facilitate communication between the patient device 150, health care provider 140, caregivers 170, 172, pharmacy 180, and possibly emergency medical service providers that expedites the delivery of appropriate care to the patient and may be critical to the patient's safety in an emergency.

In an embodiment, the physical location of the patient device 150 may be tracked by the therapy adherence application 120. When it is determined that the patient device 150 is not proximate to the patient's supply of medication or one or more monitoring devices 160, 162 that need to generate new reporting, the therapy adherence application 120 may send a message to the patient device 150 containing a reminder to the patient that the patient may need to take medication at a specific future time and/or be proximate to the at least one monitoring device 160, 162 for testing. The therapy adherence application 120 may be able to determine the distance the patient device 150 is currently away from the patient's medication supply and/or monitoring devices 160, 162 and send messages to the patient device 150 advising of the approaching treatment administration time.

In an embodiment, a patient device 150 may be equipped with accelerometer technology that allows the physical movements of the patient device 150 to be tracked. For patients with conditions in which physical movement must be closely monitored, such as asthma, measurements of the physical movement of the patient device 150 while on the patient's person over the course of a time period such as a day or a portion of a day may be used in determining the quantity and/or administration schedule of medication dosage.

In an embodiment, aspects of the therapy adherence application 120 and other components of the system 100 may be applied in enforcing dietary restriction programs, weight reduction programs, exercise regimens for healthy persons and persons in rehabilitation, drug and alcohol addiction recovery programs, smoking cessation programs, and court-mandated medication regimens for non-incarcerated sex-offenders and other offenders.

Figure 4:
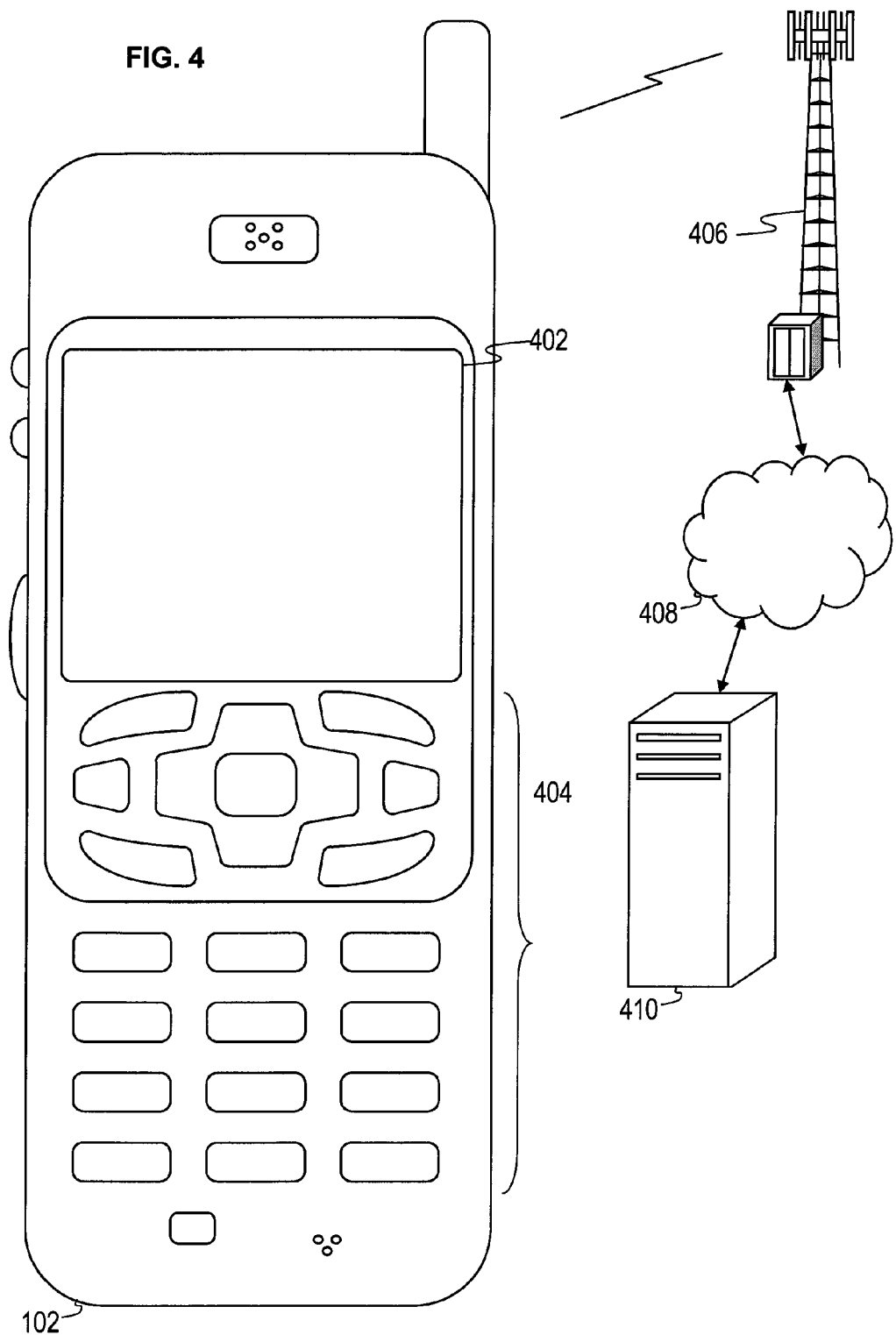
FIG. 4 is an illustration of a mobile device according to an embodiment of the disclosure.

FIG. 4 shows a wireless communications system including the mobile device 102. FIG. 4 depicts the mobile device 102, which is operable for implementing aspects of the present disclosure, for example the patient device 150, but the present disclosure should not be limited to these implementations. Though illustrated as a mobile phone, the mobile device 102 may take various forms including a wireless handset, a pager, a personal digital assistant (PDA), a gaming device, an inventory control device, a media player, a digital camera, a digital calculator, a portable computer, a tablet computer, a laptop computer, and/or other. Many suitable handsets combine some or all of these functions. In some embodiments of the present disclosure, the mobile device 102 may be a special-purpose communications device such as a mobile phone, wireless handset, pager, or PDA. The mobile device 102 may support specialized activities such as gaming, inventory control, job control, and/or task management functions, and so on.

The mobile device 102 includes a display 402 and a touch-sensitive surface or keys 404 for input by a user. The mobile device 102 may present options for the user to select, controls for the user to actuate, and/or cursors or other indicators for the user to direct. The mobile device 102 may further accept data entry from the user, including numbers to dial or various parameter values for configuring the operation of the handset. The mobile device 102 may further execute one or more software or firmware applications in response to user commands. These applications may configure the mobile device 102 to perform various customized functions in response to user interaction. Additionally, the mobile device 102 may be programmed and/or configured over-the-air, for example from a wireless base station, a wireless access point, or a peer mobile device 102.

The mobile device 102 may execute a web browser application which enables the display 402 to show a web page. The web page may be obtained via wireless communications with a base transceiver station (BTS) 406, a wireless network access node, a peer mobile device 102 or any other wireless communication network or system. While a single base transceiver station 406 is illustrated, it is understood that the wireless communication system may comprise additional base transceiver stations. In some instances, the mobile device 102 may be in communication with multiple base transceiver stations 406 at the same time. The base transceiver station 406 (or wireless network access node) is coupled to a wired network 408, such as the Internet. Via the wireless link and the wired network, the mobile device 102 has access to information on various servers, such as a server 410. The server 410 may provide content that may be shown on the display 402. Alternately, the mobile device 102 may access the base transceiver station 406 through a peer mobile device 102 acting as an intermediary, in a relay type or hop type of connection.

FIG. 5 shows a block diagram of the mobile device 102. While a variety of known components of handsets 102 are depicted, in an embodiment a subset of the listed components and/or additional components not listed may be included in the mobile device 102. The mobile device 102 includes a digital signal processor (DSP) 502 and a memory 504. As shown, the mobile device 102 may further include an antenna and front end unit 506, a radio frequency (RF) transceiver 508, an analog baseband processing unit 510, a microphone 512, an earpiece speaker 514, a headset port 516, an input/output interface 518, a removable memory card 520, a universal serial bus (USB) port 522, an infrared port 524, a vibrator 526, a keypad 528, a touch screen liquid crystal display (LCD) with a touch sensitive surface 530, a touch screen/LCD controller 532, a charge-coupled device (CCD) camera 534, a camera controller 536, and a global positioning system (GPS) sensor 538. In an embodiment, the mobile device 102 may include another kind of display that does not provide a touch sensitive screen. In an embodiment, the DSP 502 may communicate directly with the memory 504 without passing through the input/output interface 518.

The DSP 502 or some other form of controller or central processing unit operates to control the various components of the mobile device 102 in accordance with embedded software or firmware stored in memory 504 or stored in memory contained within the DSP 502 itself. In addition to the embedded software or firmware, the DSP 502 may execute other applications stored in the memory 504 or made available via information carrier media such as portable data storage media like the removable memory card 520 or via wired or wireless network communications. The application software may comprise a compiled set of machine-readable instructions that configure the DSP 502 to provide the desired functionality, or the application software may be high-level software instructions to be processed by an interpreter or compiler to indirectly configure the DSP 502.

The antenna and front end unit 506 may be provided to convert between wireless signals and electrical signals, enabling the mobile device 102 to send and receive information from a radio access network (RAN) or some other available wireless communications network or from a peer mobile device 102. In an embodiment, the antenna and front end unit 506 may include multiple antennas to support beam forming and/or multiple input multiple output (MIMO) operations. As is known to those skilled in the art, MIMO operations may provide spatial diversity which can be used to overcome difficult channel conditions and/or increase channel throughput. The antenna and front end unit 506 may include antenna tuning and/or impedance matching components, RF power amplifiers, and/or low noise amplifiers.

The RF transceiver 508 provides frequency shifting, converting received RF signals to baseband and converting baseband transmit signals to RF. In some descriptions a radio transceiver or RF transceiver may be understood to include other signal processing functionality such as modulation/demodulation, coding/decoding, interleaving/deinterleaving, spreading/despreading, inverse fast Fourier transforming (IFFT)/fast Fourier transforming (FFT), cyclic prefix appending/removal, and other signal processing functions. For the purposes of clarity, the description here separates the description of this signal processing from the RF and/or radio stage and conceptually allocates that signal processing to the analog baseband processing unit 510 and/or the DSP 502 or other central processing unit. In some embodiments, the RF transceiver 508, portions of the antenna and front end 506, and the analog baseband processing unit 510 may be combined in one or more processing units and/or application specific integrated circuits (ASICs).

The analog baseband processing unit 510 may provide various analog processing of inputs and outputs, for example analog processing of inputs from the microphone 512 and the headset 516 and outputs to the earpiece speaker 514 and the headset port 516. To that end, the analog baseband processing unit 510 may have ports for connecting to the built-in microphone 512 and the earpiece speaker 514 that enable the mobile device 102 to be used as a mobile phone. The analog baseband processing unit 510 may further include a port for connecting to a headset or other hands-free microphone and speaker configuration. The analog baseband processing unit 510 may provide digital-to-analog conversion in one signal direction and analog-to-digital conversion in the opposing signal direction. In some embodiments, at least some of the functionality of the analog baseband processing unit 510 may be provided by digital processing components, for example by the DSP 502 or by other central processing units.

The DSP 502 may perform modulation/demodulation, coding/decoding, interleaving/deinterleaving, spreading/despreading, inverse fast Fourier transforming (IFFT)/fast Fourier transforming (FFT), cyclic prefix appending/removal, and other signal processing functions associated with wireless communications. In an embodiment, for example in a code division multiple access (CDMA) technology application, for a transmitter function the DSP 502 may perform modulation, coding, interleaving, and spreading, and for a receiver function the DSP 502 may perform despreading, deinterleaving, decoding, and demodulation. In another embodiment, for example in an orthogonal frequency division multiplex access (OFDMA) technology application, for the transmitter function the DSP 502 may perform modulation, coding, interleaving, inverse fast Fourier transforming, and cyclic prefix appending, and for a receiver function the DSP 502 may perform cyclic prefix removal, fast Fourier transforming, deinterleaving, decoding, and demodulation. In other wireless technology applications, yet other signal processing functions and combinations of signal processing functions may be performed by the DSP 502.

The DSP 502 may communicate with a wireless network via the analog baseband processing unit 510. In some embodiments, the communication may provide Internet connectivity, enabling a user to gain access to content on the Internet and to send and receive e-mail or text messages. The input/output interface 518 interconnects the DSP 502 and various memories and interfaces. The memory 504 and the removable memory card 520 may provide software and data to configure the operation of the DSP 502. Among the interfaces may be the USB port 522 and the infrared port 524. The USB port 522 may enable the mobile device 102 to function as a peripheral device to exchange information with a personal computer or other computer system. The infrared port 524 and other optional ports such as a Bluetooth interface or an IEEE 802.11 compliant wireless interface may enable the mobile device 102 to communicate wirelessly with other nearby handsets and/or wireless base stations.

The input/output interface 518 may further connect the DSP 502 to the vibrator 526 that, when triggered, causes the mobile device 102 to vibrate. The vibrator 526 may serve as a mechanism for silently alerting the user to any of various events, such as an incoming call, a new text message, and an appointment reminder.

The keypad 528 couples to the DSP 502 via the input/output interface 518 to provide one mechanism for the user to make selections, enter information, and otherwise provide input to the mobile device 102. Another input mechanism may be the touch screen LCD 530, which may also display text and/or graphics to the user. The touch screen LCD controller 532 couples the DSP 502 to the touch screen LCD 530.

The CCD camera 534 enables the mobile device 102 to take digital pictures. The DSP 502 communicates with the CCD camera 534 via the camera controller 536. The GPS sensor 538 is coupled to the DSP 502 to decode global positioning system signals, thereby enabling the mobile device 102 to determine its position. In another embodiment, a camera operating according to a technology other than charge coupled device cameras may be employed. Various other peripherals may also be included to provide additional functions, e.g., radio and television reception.

FIG. 6 illustrates a software environment 602 that may be implemented by the DSP 502. The DSP 502 executes operating system drivers 604 that provide a platform from which the rest of the software operates. The operating system drivers 604 provide drivers for the handset hardware with standardized interfaces that are accessible to application software. The operating system drivers 604 include application management services ("AMS") 606 that transfer control between applications running on the mobile device 102. Also shown in FIG. 6 are a web browser application 608, a media player application 610, and JAVA applets 612. The web browser application 608 configures the mobile device 102 to operate as a web browser, allowing a user to enter information into forms and select links to retrieve and view web pages. The media player application 610 configures the mobile device 102 to retrieve and play audio or audiovisual media. The JAVA applets 612 configure the mobile device 102 to provide games, utilities, and other functionality. The patient interface and adherence application 614 corresponds to the combined functionality of the patient interface 152 and patient adherence application 154 described in the system 100.

Figure 7:
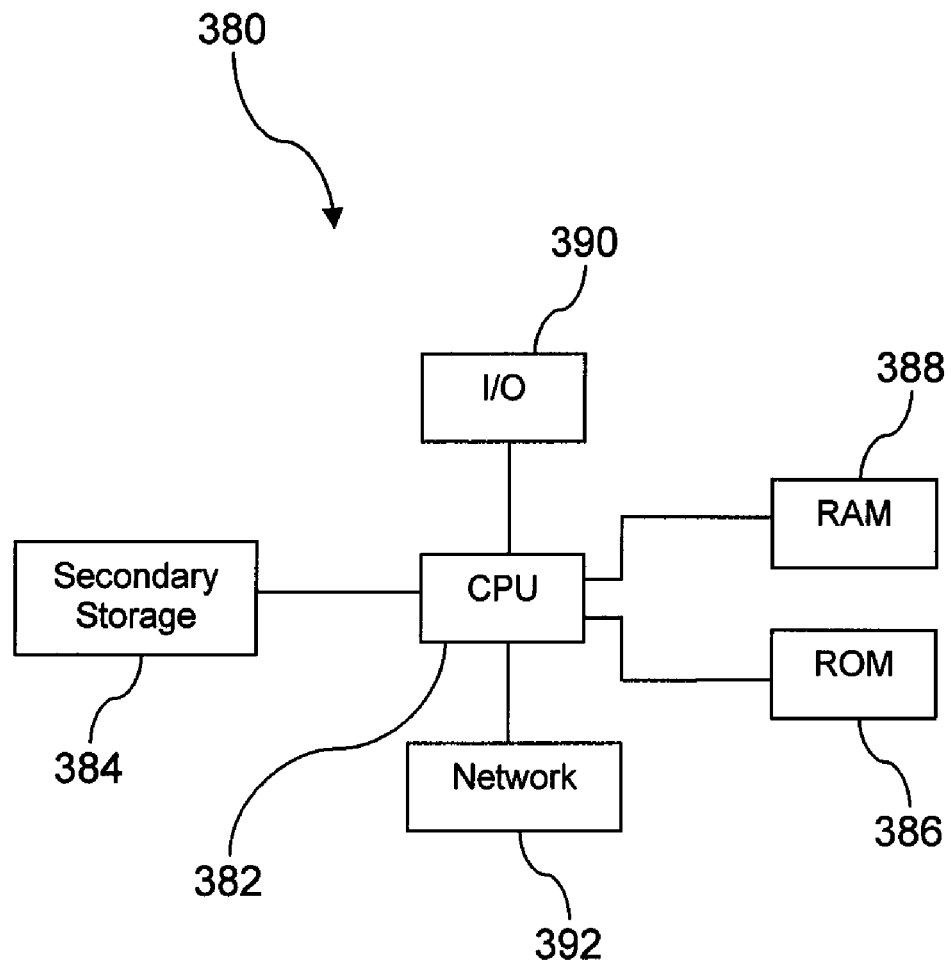
FIG. 7 illustrates an exemplary computer system suitable for implementing some aspects of the several embodiments of the disclosure.

Some aspects of the system described above may be implemented on a computer with sufficient processing power, memory resources, and network throughput capability to handle the necessary workload placed upon it. FIG. 7 illustrates a typical computer system suitable for implementing one or more embodiments disclosed herein. The computer system 380 includes a processor 382 (which may be referred to as a central processor unit or CPU) that is in communication with memory devices including secondary storage 384, read only memory (ROM) 386, random access memory (RAM) 388, input/output (I/O) devices 390, and network connectivity devices 392. The processor 382 may be implemented as one or more CPU chips.

It is understood that by programming and/or loading executable instructions onto the computer system 380, at least one of the CPU 382, the RAM 388, the ROM 386 are changed, transforming the computer system 380 in part into a particular machine or apparatus having the novel functionality taught by the present disclosure. It is fundamental to the electrical engineering and software engineering arts that functionality that can be implemented by loading executable software into a computer can be converted to a hardware implementation by well known design rules. Decisions between implementing a concept in software versus hardware typically hinge on considerations of stability of the design and numbers of units to be produced rather than any issues involved in translating from the software domain to the hardware domain. Generally, a design that is still subject to frequent change may be preferred to be implemented in software, because re-spinning a hardware implementation is more expensive than re-spinning a software design. Generally, a design that is stable that will be produced in large volume may be preferred to be implemented in hardware, for example, in an application specific integrated circuit (ASIC), because for large production runs the hardware implementation may be less expensive than the software implementation. Often a design may be developed and tested in a software form and later transformed, by well known design rules, to an equivalent hardware implementation in an application specific integrated circuit that hardwires the instructions of the software. In the same manner as a machine controlled by a new ASIC is a particular machine or apparatus, likewise a computer that has been programmed and/or loaded with executable instructions may be viewed as a particular machine or apparatus.

The secondary storage 384 is typically comprised of one or more disk drives or tape drives and is used for non-volatile storage of data and as an over-flow data storage device if RAM 388 is not large enough to hold all working data. Secondary storage 384 may be used to store programs which are loaded into RAM 388 when such programs are selected for execution. The ROM 386 is used to store instructions and perhaps data which are read during program execution. ROM 386 is a non-volatile memory device which typically has a small memory capacity relative to the larger memory capacity of secondary storage 384. The RAM 388 is used to store volatile data and perhaps to store instructions. Access to both ROM 386 and RAM 388 is typically faster than to secondary storage 384.

I/O devices 390 may include printers, video monitors, liquid crystal displays (LCDs), touch screen displays, keyboards, keypads, switches, dials, mice, track balls, voice recognizers, card readers, paper tape readers, or other well-known input devices.

The network connectivity devices 392 may take the form of modems, modem banks, Ethernet cards, universal serial bus (USB) interface cards, serial interfaces, token ring cards, fiber distributed data interface (FDDI) cards, wireless local area network (WLAN) cards, radio transceiver cards such as code division multiple access (CDMA), global system for mobile communications (GSM), and/or worldwide interoperability for microwave access (WiMAX) radio transceiver cards, and other well-known network devices. These network connectivity devices 392 may enable the processor 382 to communicate with an Internet or one or more intranets. With such a network connection, it is contemplated that the processor 382 might receive information from the network, or might output information to the network in the course of performing the above-described method steps. Such information, which is often represented as a sequence of instructions to be executed using processor 382, may be received from and outputted to the network, for example, in the form of a computer data signal embodied in a carrier wave.

Such information, which may include data or instructions to be executed using processor 382, for example, may be received from and outputted to the network, for example, in the form of a computer data baseband signal or signal embodied in a carrier wave. The baseband signal or signal embodied in the carrier wave generated by the network connectivity devices 392 may propagate in or on the surface of electrical conductors, in coaxial cables, in waveguides, in optical media, for example optical fiber, or in the air or free space. The information contained in the baseband signal or signal embedded in the carrier wave may be ordered according to different sequences, as may be desirable for either processing or generating the information or transmitting or receiving the information. The baseband signal or signal embedded in the carrier wave, or other types of signals currently used or hereafter developed, referred to herein as the transmission medium, may be generated according to several methods well known to one skilled in the art.

The processor 382 executes instructions, codes, computer programs, scripts which it accesses from hard disk, floppy disk, optical disk (these various disk based systems may all be considered secondary storage 384), ROM 386, RAM 388, or the network connectivity devices 392. While only one processor 382 is shown, multiple processors may be present. Thus, while instructions may be discussed as executed by a processor, the instructions may be executed simultaneously, serially, or otherwise executed by one or multiple processors.

While several embodiments have been provided in the present disclosure, it should be understood that the disclosed systems and methods may be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted or not implemented.

Also, techniques, systems, subsystems, and methods described and illustrated in the various embodiments as discrete or separate may be combined or integrated with other systems, modules, techniques, or methods without departing from the scope of the present disclosure. Other items shown or discussed as directly coupled or communicating with each other may be indirectly coupled or communicating through some interface, device, or intermediate component, whether electrically, mechanically, or otherwise. Other examples of changes, substitutions, and alterations are ascertainable by one skilled in the art and could be made without departing from the spirit and scope disclosed herein.

What is claimed is:

1. A therapy adherence system, comprising:
   an at least one computer system;
   a database; and
   an application that, when executed on the at least one computer system,
      receives a message from a home-based patient device containing medication compliance information and physical condition information;
      compares medication compliance information and physical condition information with a current treatment regimen and historical medication and physical condition information stored in the database;
      calculates an updated regimen and an initial health risk level based on at least current and historical medication compliance information and physical condition information;
      notifies an at least one health care provider when the initial health risk level exceeds a threshold;
      receives a response from the at least one health care provider, the response comprising adjustments to the updated regimen and a diagnosis;
      communicates the updated regimen;
      calculates a subsequent risk level based upon data from at least one of the patient and the home-based patient monitoring device;
      when the subsequent risk level is higher than the initial health risk level, sends alerting notifications with at least one of increased frequency and increased intensity to the at least one healthcare provider;
      when the at least one health care provider does not timely respond to the alerting notifications, contacts an emergency medical provider or a law enforcement agency.

2. The system of claim 1, wherein the at least one health care provider comprises at least one of a physician, an in-home health care provider, a visiting nurse service, and a pharmacy.

3. The system of claim 1, wherein the system encourages regimens for treatment of at least one of chronic illness and disability and regimens for weight control, diet, and exercise programs, and compliance with court-imposed requirements.

4. The system of claim 1, wherein the system compiles historical records on patient conditions, medical data, and medication regimen compliance on a plurality of patients.

5. The system of claim 4, wherein the system uses the historical data to infer health trends in individual patients and provides the trend information to the patients' health care providers for health care providers' use in diagnosing conditions and adjusting regimens.

6. The system of claim 4, wherein the historical data is aggregated, subjected to statistical analysis, and made available to pharmaceutical manufacturers, universities, and government agencies for use in determining efficacy of medication and treatment regimens.

7. The system of claim 4, wherein the application more frequently determines a health risk level using different criteria as the health risk level rises.

8. The system of claim 4, wherein the application further contacts at least one caregiver prior to notifying the at least one health care provider.

9. A processor-implemented method of encouraging therapy regimen adherence, comprising:
   a therapy adherence server receiving a first message from a patient device, the first message comprising patient medication regimen compliance information;
   the therapy adherence server reviewing the patient medication regimen compliance information received in the first message from the patient device against a current prescribed medication regimen to determine variances from the prescribed patient medication regimen;
   the therapy adherence server entering the received patient medication regimen compliance information into a database;
   the therapy adherence server determining an adjusted patient medication regimen adjusting at least one of dosage of medication prescribed and schedule for administering medication;
   the therapy adherence server sending a second message containing the adjusted patient medication regimen to the patient device;
   the therapy adherence server setting a timer to track compliance with the adjusted patient medication regimen, wherein the timer is set to conduct follow-up messaging with the patient device;
   the therapy adherence server determining an initial patient risk level and a subsequent patient risk level;
   the therapy adherence server sending alerting notifications with at least one of increased frequency and increased intensity to at least one health care provider when the subsequent patient risk level is higher than the initial patient risk level; and
   the therapy adherence server contacting an emergency medical provider or a law enforcement agency when the at least one health care provider does not timely respond to the alerting notifications.

10. The method of claim 9, wherein the patient device is one of a mobile telephone and personal digital assistant (PDA) and the patient device is enabled for near-field communication.

11. The method of claim 10, wherein the patient device receives messaging from at least one patient monitoring device and the messaging comprises at least one of patient vital signs, body temperature, pulse rate, blood chemistry information, glucose level information, saliva chemistry information, and blood pressure information.

12. The method of claim 11, wherein information contained in the messaging from the patient monitoring devices is stored in a database.

13. The method of claim 9, wherein when the medication regimen comprises a plurality of medications and the patient does not comply with the regimen for at least a first medication, the method adjusts the dosage quantity and administration schedule for at least one of the other medications in the regimen.

14. The method of claim 9, wherein the method contacts caregivers comprising at least one of family members, counselors, and court-appointed officers.

15. The method of claim 9, wherein the method increases at least one of the frequency and intensity of alerting notifications sent to the patient device when expected messages are not received from the patient device by scheduled deadlines.

16. A processor-implemented method of encouraging therapy regimen adherence, comprising:
   a therapy adherence server receiving a first message from a patient device;
   the therapy adherence server calculating compliance with a medication regimen;
   the therapy adherence server determining a first risk level of patient condition;

the therapy adherence server sending a second message to at least one care provider, the second message containing the first risk level determined based on current and historical information on the patient;

the therapy adherence server determining a second risk level of patient condition;

the therapy adherence server sending a plurality of messages to the at least one care provider with increased frequency and intensity when the second risk level is higher than the first risk level; and the therapy adherence server contacting an emergency medical provider or a law enforcement agency when the at least one care provider does not timely respond to the plurality of messages.

17. The method of claim 16, wherein messages are sent to the patient containing inquiries about symptoms experienced.

18. The method of claim 16, wherein the method contacts a pharmacy for refill of medication.

19. The method of claim 16, wherein the method further includes tracking the physical location of a patient device and communicating alerts to the patient device when the patient device is determined to be physically distant from medication and monitoring devices.

20. The method of claim 16, wherein the patient is at least one of a homebound senior citizen, homebound veteran, mentally or physically disabled person, minor, eating-disorder patient, grossly overweight person, and parolee or registered sex-offender subject to at least one of court-ordered home confinement and medication regimen.

* * * * *